United States Patent
Stowasser (10) Patent No.: US 12,254,973 B2
(45) Date of Patent: Mar. 18, 2025

(54) COMPUTER-IMPLEMENTED METHOD FOR PROVIDING AN OUTPUT DATA SET

(71) Applicant: Siemens Healthcare GmbH, Erlangen (DE)

(72) Inventor: Boris Stowasser, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 424 days.

(21) Appl. No.: 17/092,203

(22) Filed: Nov. 6, 2020

(65) Prior Publication Data
US 2021/0142889 A1    May 13, 2021

(30) Foreign Application Priority Data
Nov. 7, 2019  (DE) .................... 10 2019 217 220.2

(51) Int. Cl.
*G06T 5/50*      (2006.01)
*G06N 20/00*    (2019.01)
(Continued)

(52) U.S. Cl.
CPC ............. *G16H 30/40* (2018.01); *G06N 20/00* (2019.01); *G06T 3/40* (2013.01); *G06T 5/50* (2013.01);
(Continued)

(58) Field of Classification Search
CPC .......... G16H 30/40; G06N 20/00; G06T 3/40; G06T 75/002; G06T 5/50
See application file for complete search history.

(56) References Cited

U.S. PATENT DOCUMENTS

| | | | |
|---|---|---|---|
| 11,574,170 B2 * | 2/2023 | Isogawa | ................ G06N 3/084 |
| 2010/0272340 A1 | 10/2010 | Bar-Aviv | |

(Continued)

FOREIGN PATENT DOCUMENTS

| | | |
|---|---|---|
| CN | 103218777 A | 7/2013 |
| CN | 107106105 A | 8/2017 |

(Continued)

OTHER PUBLICATIONS

Cerciello, Tommaso, et al. "A comparison of denoising methods for X-ray fluoroscopic images." Biomedical Signal Processing and Control 7.6 (2012): 550-559.

(Continued)

*Primary Examiner* — Edward Park
(74) *Attorney, Agent, or Firm* — Lempia Summerfield Katz LLC (57) ABSTRACT

A method for providing an output data set as a function of an input data set includes applying an algorithm for reducing image noise to the input data set or an intermediate data set determined as a function of the input data set to determine a noise-reduced signal data set. The method includes determining a noise data set as difference between the input data set or the intermediate data set and the signal data set. The method includes determining a modified noise data set by applying a noise-processing algorithm to the noise data set and/or determining a modified signal data set by applying a signal processing algorithm to the signal data set. The method includes determining an output data set by adding the modified noise data set to the signal data set or the modified signal data set, or adding the noise data set to the modified signal data set.

15 Claims, 7 Drawing Sheets

(51) Int. Cl.
  *G06T 3/40* (2006.01)
  *G06T 5/70* (2024.01)
  *G16H 30/40* (2018.01)
  *G06N 3/084* (2023.01)

(52) U.S. Cl.
  CPC ............... *G06T 5/70* (2024.01); *G06N 3/084* (2013.01); *G06T 2207/20016* (2013.01); *G06T 2207/20081* (2013.01); *G06T 2207/20084* (2013.01); *G06T 2207/20224* (2013.01)

(56) References Cited

U.S. PATENT DOCUMENTS

| | | |
|---|---|---|
| 2011/0097008 A1 | 4/2011 | Cao |
| 2013/0064470 A1* | 3/2013 | Suzuki .................. G06V 10/30 382/274 |
| 2013/0188847 A1 | 7/2013 | Zou |
| 2016/0019702 A1* | 1/2016 | Park ...................... G06T 11/008 382/131 |
| 2017/0165008 A1 | 6/2017 | Finley |
| 2017/0278225 A1* | 9/2017 | Nishimura .............. G06T 5/002 |
| 2018/0204306 A1 | 7/2018 | Brendel |
| 2019/0035058 A1 | 1/2019 | Strobel |
| 2019/0035118 A1* | 1/2019 | Zhao ...................... G06T 11/008 |
| 2019/0137589 A1* | 5/2019 | Noguchi ................ A61B 6/032 |
| 2020/0118250 A1* | 4/2020 | Takahama ............... G06T 5/002 |
| 2020/0211161 A1* | 7/2020 | Trejo ........................ G06T 5/20 |
| 2021/0142889 A1* | 5/2021 | Stowasser ............... G06T 5/009 |
| 2022/0330920 A1* | 10/2022 | Sato ..................... A61B 8/5207 |

FOREIGN PATENT DOCUMENTS

| | | |
|---|---|---|
| EP | 2238742 B1 | 5/2014 |
| WO | 2011161557 A1 | 12/2011 |

OTHER PUBLICATIONS

Foi, Alessandro. "Clipped noisy images: Heteroskedastic modeling and practical denoising." Signal Processing 89.12 (2009): 2609-2629.

German Office Action for German Application No. 10 2019 217 220.2 dated Sep. 10, 2020.

\* cited by examiner

COMPUTER-IMPLEMENTED METHOD FOR PROVIDING AN OUTPUT DATA SET

This application claims the benefit of German Patent Application No. DE 10 2019 217 220.2, filed on Nov. 7, 2019, which is hereby incorporated by reference in its entirety.

BACKGROUND

The present embodiments relate to providing an output data set as a function of an input data set that is determined by a medical imaging method. In addition, the present embodiments relate to data processing in the context of medical subtraction imaging.

Significantly different contrasts and noise amplitudes may occur in image data from medical imaging methods due to numerous factors (e.g., as a function of the mapped examination object, the specific examination performed, the imaging parameters, etc.), which may complicate the evaluation of the image data. This problem may, for example, occur with modern approaches to dose regulation with which the X-ray parameters (e.g., tube voltage, tube current, exposure time, and aperture and/or focus parameters) are regulated as a function of the contrast-to-noise ratio for a specific object. Additional parameters to be taken into account in this case may, for example, be the water equivalent, the size of the object, which is relevant in respect of spatial frequencies, the measuring speed, and the material of the object.

Although the procedure described may reduce the examination object's exposure to radiation, the image noise, which is, for example, dose-dependent, and the object's contrast, which is, for example, a function of the tube voltage, are no longer constant parameters and change with a variable water equivalent, for example. Herein, the water equivalent designates a dose regulation parameter that correlates with the patient thickness and may be interpreted as a measure for an equivalent water layer. The image noise in the image is also a function of the dose distribution on the detector, where very high local differences may occur.

From the user's viewpoint, constant noise is desirable both within an image (e.g., both in regions with low absorption and regions with high absorption) and between different images (e.g., in images of different patients or for different angulations). In some circumstances, contrast adjustment is also desirable in order to achieve the same contrasts with the same object thicknesses of the same material, as this facilitates evaluation of the image data.

It is in principle known in the prior art to reduce image noise (e.g., by filtering). In this case, a low-pass filter or Gaussian filter may be used to filter spatial frequencies or for temporal filtering of high frequencies.

Various approaches for noise reduction in X-ray images are, for example, discussed in the publication CERCIELLO, T. et. al.: "A comparison of denoising methods for X-ray fluoroscopic images," in: Biomedical Signal Processing and Control, 2012, Vol. 7, pp. 550-559. In this case, two classes of algorithms are used in order to reduce noise. One class serves to suppress signal-dependent noise and the other serves to eliminate signal-independent noise. In this case, it has been established that algorithms for removing signal-dependent noise supply better results overall.

The publication Foi, A.: "Clipped noisy images: Heteroskedastic modeling and practical denoising," in: Signal Processing. 2009, Vol. 89, No. 12, pp. 2609-2639, teaches a two-stage approach to noise reduction. In this case, initially, a variance-stabilizing transformation is applied to the image data; after this, a filter is used for signal-independent noise in order to suppress noise. This is followed by an inverse transformation in order to cancel the variance stabilization.

However, noise reduction is subject to narrow limits since excessive noise reduction may result in an unnatural image impression and may falsify the image data or generate artifacts. This may complicate a subsequent diagnosis.

As a further complicating factor, any contrast adjustment, in order, for example, to compensate changes in contrast resulting from dose regulation, may lead to a change in the noise spectrum that places narrow limits on the provision of a similar image impression for images recorded with dose regulation (e.g., on different patients) or for different angulations. Therefore, in order to avoid a highly variable image impression within one image or when comparing different images, it may be necessary to restrict dose regulation so that it is not possible to use the actually most efficient dose regulation for a specific imaging task in all cases.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved approach for processing image data from medical imaging methods that enables a viewer to obtain more similar image impressions compared to pure noise reduction even with greatly varying imaging parameters is provided.

A computer-implemented method for providing an output data set as a function of an input data set, which is determined by a medical imaging method, includes applying an algorithm for reducing image noise to the input data set or an intermediate data set determined as a function of the input data set to determine a noise-reduced signal data set. A noise data set is determined as a difference between the input data set or the intermediate data set and the signal data set. A modified noise data set is determined by applying a noise-processing algorithm to the noise data set, and/or a modified signal data set is determined by applying a signal processing algorithm to the signal data set. An output data set is determined by adding the modified noise data set to the signal data set or the modified signal data set, or by adding the noise data set to the modified signal data set.

The present embodiments are based on the idea of separately processing the noise component and the signal component of an input data set or an intermediate data set determined therefrom by preprocessing and recombining the noise component and the signal component after the separate processing. This enables the signal data set, and hence, for example, the contrast and the noise to be changed at least approximately independently of one another. As a result of this, a desired image impression may be more closely approximated, or a desired image impression may continue to be achieved even though additional degrees of freedom for dose regulation are opened up.

In this case, the desired image impressions (e.g., a strength of a noise, a spectral composition of a noise, contrasts that occur in the image, etc.) may, for example, be fixed, or the desired image impressions may also be established according to the preference of a specific user (e.g., an evaluating physician). Hence, the method according to the present embodiments support an evaluator in the evaluation of the image data from the medical imaging method since, for example, a more uniform image impression may be achieved within an image and/or better comparability of different images, which have, for example, been recorded for different examination objects or from different angulations, may be achieved. At the same time, it is potentially possible to reduce the exposure of an examination object since it is also possible to permit dose regulation that, without the use of the method according to the present embodiments, would result in an excessively non-uniform image impression and hence render a meaningful evaluation of the image data impossible or least greatly complicate the evaluation.

The signal processing cycle and/or the noise-processing algorithm may be functions of the specific imaging parameters. The signal processing cycle and/or the noise-processing algorithm may be functions of object parameters of the examination object (e.g., the weight and/or water equivalent and/or the size of the examination object). Supplementarily or alternatively, the processing cycle and/or the noise-processing algorithm may be functions of imaging parameters or output variables of the dose regulation (e.g., a tube voltage, a tube current, an exposure time, and/or aperture, and/or focus settings).

The input data may, for example, be X-ray images that may, for example, be recorded by a flat-panel detector. The input data sets may describe two-dimensional or three-dimensional image data. The following primarily discusses, by way of example, X-ray imaging as a medical imaging method since the method according to the present embodiments may be used particularly advantageously in combination with the use of dose regulation. In principle, however, the method according to the present embodiments may also be used in other fields of medical imaging (e.g., for magnetic resonance tomography data, positron emission tomography data, and the like). In the context of X-ray imaging, the method according to the present embodiments may serve to process two-dimensional image data. This may in principle also entail individual projection images from a computed tomography scanner that are combined to form a three-dimensional image presentation.

In a variant of the method according to the present embodiments, input data sets including a plurality of sequentially recorded image data sets are processed. This enables the algorithm for reducing the image noise to process a plurality of these image data sets jointly in order, for example, to perform temporal filtering and hence, for example, to suppress a temporally high-frequency noise using a temporal low-pass or Gaussian filter. Regardless of whether the input data set includes a plurality of sequentially recorded image data sets, the algorithm for reducing the image noise may, for example, perform a filtering of spatial frequencies (e.g., with a low-pass filter or a Gaussian kernel). Algorithms that are known per se (e.g., the algorithms named in the publications cited in the introduction) may be used to reduce image noise. However, as will be explained later, it is also possible to train the algorithm using a machine-learning method.

The noise-processing algorithm may include scaling of the noise data set or different scaling of different frequency components of the noise data set or filtering of the noise data set. The measures named may achieve a uniform desired image impression with respect to noise. Changing the frequency composition of the noise by different scaling of different frequency components or filtering achieves noise shaping, thus enabling, for example, a desired noise coloration or noise decoloration to be achieved.

If, as explained above, the input data set includes a plurality of sequentially acquired image data sets, the scaling of different frequency components or the filtering of the noise data set may be based on the temporal frequency composition of the noise. Independently thereof, the composition of the noise data set may also be changed with respect to the spatial frequencies by corresponding filtering or scaling of different frequency components of the spatial frequencies.

A different scaling of different frequency components may, for example, be implemented in that the noise data set is Fourier transformed and then multiplied by an envelope in the frequency space. Alternatively, the envelope may be inverse transformed in the frequency space and convolution may be performed there. It may, however, be more efficient to apply Gaussian kernels of different sizes and calculate the difference between the resulting data to construct a Gauss-Laplace pyramid; individual layers of the Gauss-Laplace pyramid correspond to different frequency components.

The scaling factor or different scaling factors or filter parameters for the filtering may be fixed or also set by a user or service technician. However, these variables may be functions of the aforementioned imaging parameters or, for example, of the image data from the actual input data set as will be explained in more detail later.

At least one measure for noise in the input data set or the intermediate data set or the noise data set may be determined, where the noise-processing algorithm is a function of the measure for the noise. In the context of the method according to the present embodiments, the noise is, for example, to be set to a prespecified target impression. Therefore, the noise may be quantified, and the noise may then be modified such that desired properties of the noise are achieved.

If the data set under consideration substantially exclusively contains noise, which may be, for example, achieved for the noise data set, the amplitude of the image data or, for example, also the standard deviation of the image data may be used as a measure for the noise.

However, if the evaluated image data includes both a signal component and a noise component (e.g., if the input data set is evaluated directly or a variance-stabilized, intermediate data set is evaluated), it is advantageous in the context of the determination of the measure for the noise to attempt to separate out the signal component at least to a large extent. For this, it is, for example, possible for a histogram of the image data to be evaluated, and it is possible, for example, based on a focal point or peak of this histogram, only to take account of values lying within a prespecified region. The prespecified region may, for example, be specified as a function of the standard deviation, which may also be determined from the histogram or from the image data. For example, it is possible to take account of all values with a distance from the focal point or peak of the histogram corresponding at the most to five times the standard deviation. If, for example, a standard deviation of the distance from the focus or peak or also another a measure (e.g., a norm) for this deviation is calculated for such values, preliminary tests have shown this represents a good measure for the noise in the image data set under consideration.

The measure for the noise may, for example, be used to parameterize the above-explained scaling, frequency-dependent scaling, or filtering. The scaling factor for the scaling of the noise data set or the scaling factors for the scaling of the frequency components and/or a parameter of the filtering may be determined as a function of the at least one measure for the noise.

This, for example, enables the amplitude of the noise or individual frequency components of the noise to be set to a desired value, thus enabling a desired image impression to be achieved in respect of the noise. If filtering is parameterized or a plurality of frequency components are scaled, it is, for example, possible to determine a plurality of measures for the noise. For example, separate measures are calculated for different frequency components of the noise. Alternatively, the frequency distribution of the noise may be taken into account in a different way (e.g., in that, in addition to the strength of the noise, a coloration of the noise is determined). This may then be compensated by corresponding filtering or weighting of frequency components, or a desired coloration may be set.

The connection between the measure or the measures for the noise and the scaling factor or the scaling factors or the filtering parameter may be defined by a prespecified connection (e.g., a lookup table or target function). For example, the connection may be prespecified such that at least one measure for the noise in the noise data set is set at least approximately to a prespecified value. The connection (e.g., the lookup table) may take account of additional parameters in order, for example, to take account of parameters of the X-ray imaging, the examination object, or user settings and/or preferences. For example, it is additionally possible to take account of a patient's water equivalent or a user-selectable image impression.

The intermediate data set may be determined by applying a variance-stabilizing transformation to the input data, where the signal processing algorithm is or includes an assigned inverse transformation. In this case, it is, for example, possible that no inverse transformation is performed for the noise data set; as a result of this, the noise in the output data set may, for example, remain substantially independent of the signal amplitudes.

As already mentioned in the introduction, in X-ray imaging, a distinction may be made between signal-independent noise, which is, for example, caused by noise from the measurement electronics, and signal-dependent noise, which occurs due to the quantum behavior of the incident photons. In most cases, the signal-dependent (e.g., Poisson-distributed) noise component predominates. The application of a variance-stabilizing transformation (e.g., an Anscombe transformation or also the application of a square root to the image data) may at least approximately eliminate the signal dependence of the noise and achieve signal-independence of the noise.

This enables the algorithm for reducing image noise to be configured to reduce signal-independent noise. This provides that it is possible to apply a large number of known algorithms and even new algorithms (e.g., trained by machine learning) may potentially be simpler to construct. At the same time, it may be achieved in this way that signal-independent noise is achieved in the noise data set, and hence, ultimately, also in the output data set, which is typically perceived as more pleasant by evaluators of corresponding data sets or facilitates the evaluation. For example, this avoids extremely different noise being mapped in regions with strong and low absorption.

The application of inverse transformation in the context of the signal processing algorithm has the result that the modified signal data set, and hence, also the output data set relating to the signals, is not falsified by this variance-stabilizing transformation. Variance-stabilizing transformations and inverse transformations are known in principle and therefore do not need to be explained in detail. By way of example, reference is made in this regard to the publication by A. Foi already cited in the introduction.

The signal processing algorithm may, for example, include a gray level transformation. For example, in the context of the signal processing algorithm, a non-linear function (e.g., a logarithmic function) may be applied to the image data from the signal data set or the image data from of a processing result determined in the context of preprocessing within the signal processing algorithm as a function of the signal data set. The preprocessing may, for example, be the above-explained inverse transformation for variance-stabilizing transformation.

The application of a logarithmic function may be provided since, due to the exponential law of attenuation, in X-ray imaging, the same object thickness differences with the same material in the examination object result in the same contrast differences. This greatly facilitates the evaluation of the image data. However, in some cases, it may also be advantageous to deviate from the logarithmic function (e.g., for particularly low or particularly high intensities). In addition, scattered radiation correction may take place, as will be explained later.

The non-linear function may, for example, be prespecified as a lookup table or also as an analytical function. In addition, the non-linear function may be a function of further parameters. For example, parameters of dose regulation or X-ray imaging generally, parameters of the examination object, or user settings may be taken into account.

In one embodiment, a contribution of scattered radiation that occurs during the acquisition of the input data set to the image data from the signal data set or the processing result is predicted. The non-linear function is a function of the predicted contribution, or the signal data set or the intermediate result is corrected before the application of the non-linear function as a function of the predicted contribution. The contribution may, for example, be an offset that is subtracted from the signal data set or the processing result before the application of the non-linear function used to modify the non-linear function.

It is, for example, important to take account of scattered radiation when the method according to the present embodiments is used to generate items of image data that are to be directly compared with one another or when there is to be a reconstruction of three-dimensional image data from two-dimensional image data from the output data set or a plurality of output data sets. Since different contributions of the scattered radiation and hence, for example, different offsets potentially occur in the plurality of images, artifacts may result in a reconstruction of three-dimensional image data, or the comparison of two-dimensional or three-dimensional image data sets may be complicated. If the method is applied to one single image data set, it may nevertheless be advantageous to take account of scattered radiation since, for example, it is possible achieve better comparability of different examinations.

The prediction of a scattered radiation contribution is in principle known in the prior art and does not need to be explained in detail. For example, the scattered radiation is a function of patient properties that may be taken into account with reference to a detailed patient model or also by one or more individual parameters (e.g., water equivalent or weight). In addition, imaging parameters (e.g., dose-regulation parameters) are relevant. Corresponding connections may be determined by preliminary tests and, for example, acquired statistically. The corresponding connections may then, for example, be filed in a lookup table, or it is possible to determine a functional connection between the parameters taken into account and the probable occurrence of scattered radiation or a contribution to the image data resulting therefrom (e.g., by a regression analysis).

In the context of the signal processing algorithm, a function for contrast adjustment may be applied to the image data from the signal data set or the image data from a processing result or a further processing result, which is determined in the context of preprocessing within the signal processing algorithm as a function of the signal data set. In this case, the processing result may be the result of the application of the non-linear function or inverse transformation to the signal data set. A further processing result may, for example, be further processed if both inverse transformation and the non-linear function have been applied to the signal data set.

Approaches for contrast adjustment in image data sets are in principle known in the prior art, and therefore, there will only be a brief discussion of a few examples in the following. In this case, the essential difference from the usual procedure in the method according to the present embodiments is that the contrast adjustment takes place in the context of the signal processing algorithm and hence substantially independently of the noise component of the input data set. Subsequent addition of the noise data set or the modified noise data set causes the noise component of the output data set to be at least approximately independent of the contrast adjustment, thus achieving the advantage compared to the usual procedure that a contrast adjustment does not result in shaping or coloration of the noise, which may disrupt or falsify an image impression.

The function for contrast adjustment may include gray level transformation and/or weight different frequency components of the signal data set, or the processing result or the further processing result to different degrees. For example, high frequency components may be emphasized or suppressed in order to highlight or suppress fine structures.

The function for contrast adjustment may be fixed; however, the function may be a function of imaging parameters (e.g., parameters used in the context of X-ray imaging such as tube voltage, tube current, exposure time, and/or aperture or focus setting). Supplementarily or alternatively, the function for contrast adjustment may be a function of user settings in order to adjust the contrast to the wishes of a user (e.g., an image evaluator). It is also possible for parameters relating to the examination object (e.g., water equivalent, image content of the processed data set, and/or the type of examination) to be taken into account in order to prespecify or parameterize the function.

In the method according to the present embodiments, the signal processing algorithm and/or the noise-processing algorithm may be parameterized as a function of at least one input parameter and/or at least one output variable of dose regulation used in the context of the medical imaging method. The input parameters or output variables may be provided directly by the imaging device. This may, for example, be advantageous when the computer-implemented method is to be used in the context of a first examination of the measurements data or an immediate evaluation. However, it is also possible for the at least one input parameter or the at least one output variable to be stored together with the input data set (e.g., in an image database) or provided in some other way together with the input data set for processing by the computer-implemented method. Hence, in this case, the computer-implemented method may also be performed separately from the acquisition of the measurement data (e.g., also on a separate device or by another service provider).

Input parameters for dose regulation may, for example, be parameters of the examination object (e.g., a patient), such as, for example, water equivalent, weight, dimensions, or the like. Supplementarily or alternatively, it is also possible for measurement data acquired during the acquisition of the input data set to be taken into account (e.g., a currently acquired dose, contrast and/or image noise, such as a contrast-to-noise ratio for a specific object, or the like).

The output variables taken into account may, for example, be the tube current, tube voltage, exposure time and/or filter, aperture, and/or focus settings.

Various parameters of the noise-processing algorithm or the signal processing algorithm or processing acts that may be performed in the context of these algorithms have already been explained above.

The algorithm used to reduce the image noise may be an algorithm trained by a machine-learning method. Such an algorithm may, for example, be or include a neural network, a support vector machine, a decision tree, and/or a Bayesian network. Alternatively or supplementarily, the trained algorithm may also be based on a k-means algorithm, Q-learning, a genetic algorithm, and/or association rules. A neural network may, for example, be a deep neural network, a convolutional neural network, or a convolutional deep neural network. Supplementarily or alternatively, the neural network may be an adversarial network, a deep adversarial network, and/or a generative adversarial network.

The algorithm may be trained by supervised learning, partially supervised learning, reinforcement learning, active learning, and/or unsupervised learning.

For example, the algorithm may be trained using training data sets that each include a first image data set and a second image data set, which may have been acquired on the same examination object with the same acquisition parameters. For the training of the algorithm, it is possible to minimize a cost function that is a function of a difference between a measure for the noise in the first image data set and a measure for the noise in a sum data set, where the sum data set is determined in that the algorithm to be trained is applied to the second image data set and the resultant result data set is added to the first image data set. Minimization of the cost function may take place by varying parameters of the algorithm to be trained for which purpose it is, for example, possible to use error feedback that is known per se.

The described method for training the algorithm for reducing image noise exploits the fact that image noise in different images is independent and so the variances caused by the noise are at least approximately added together. If a measure for the noise (e.g., the variance) in the total image is the same as the measure for the noise in the first image data set, this is an indication that the application of the algorithm has substantially completely eliminated the noise in the second image data set.

Although the training of the algorithm may in principle be part of the method according to the present embodiments, in the method according to the present embodiments, an algorithm that was trained before the start of the method according to the present embodiments may be used to reduce image noise. Hence, the present embodiments also relate to a method for training an algorithm for reducing image noise. In addition, the present embodiments relate to a training apparatus configured to carry out this method, a program that performs the acts of this method when executed on a data processing device, and a computer-readable data carrier that stores such a program. The present embodiments also relate to a trained algorithm for reducing image noise or parameter data sets that parameterize a prespecified algorithm for providing this algorithm, or to a computer-readable data carrier (e.g., a non-transitory computer-readable storage medium) that stores the algorithm or the parameters thereof. The algorithm or the parameters thereof, and hence also the data carrier, may, for example, be provided as the product of the explained training method.

In addition to the computer-implemented method for providing an output data set, the present embodiments relate to a computer-implemented method for data processing in the context of medical subtraction imaging, where two input data sets are processed. The two input data sets are each determined by a medical imaging method on the same examination object. The method includes the following acts: applying the computer-implemented method according to the present embodiments for providing an output data set to the input data sets in order to determine a respective output data set; subtracting the output data sets from one another in order to provide a subtraction data set; and applying a function for contrast adjustment to the image data from the subtraction data set.

In other words, the method according to the present embodiments for providing an output data set with which a noise data set and a signal data set are processed separately is applied separately to these input data sets before the subtraction of the input data sets. After the subtraction, contrast adjustment is performed. For example, in the context of the preprocessing of the input data sets (e.g., in the context of the signal processing algorithm), initially, no contrast adjustment may take place since this may potentially have the result that an offset occurs in a relevant region or the like during the determination of the subtraction data set. For example, in the context of the signal data processing, initially, exclusively inverse transformation may be applied if variance stabilization was performed previously and optionally a non-linear function was applied (e.g., a logarithmic function).

The subsequent contrast adjustment of the image data from the subtraction data set may take place in the same way, as explained above with regard to the contrast adjustment in the context of signal data processing and/or the parameters mentioned in this regard. Although shifting the contrast adjustment to a later time point in the processing at which the noise data set or the modified noise data set, and the signal data set or the modified signal data set have already been combined causes the contrast adjustment to act not only on the signal component but also on the noise component of the image data, this is acceptable if only relatively mild contrast adjustments take place. Shifting parts of the change in the signal component into the signal processing algorithm (e.g., the application of a logarithm by which the signal component is significantly changed) may nevertheless achieve a lower influence on the noise component than in cases in which the noise component and the signal component are continuously processed jointly.

In addition to the explained computer-implemented method, the present embodiments relate to a provisioning device that is configured to execute the computer-implemented method according to the present embodiments for providing an output data set and/or the computer-implemented method for data processing in the context of medical subtraction imaging. For example, the provisioning device may include an input interface to receive the input data set or input data sets and an output interface to output the output data set or the contrast-adjusted subtraction data set. The provisioning device may be embodied as a data processing device configured to carry out the data processing explained in relation to the method. The data processing may, for example, be performed by a correspondingly programmed processor (e.g., a microprocessor, microcontroller, FPGA, DSP or the like) or also in a distributed manner by a large number of processors (e.g., by a cloud).

The features explained with respect to the computer-implemented method according to the present embodiments and the advantages mentioned may be transferred to the provisioning device according to the present embodiments and vice versa.

In addition, the present embodiments relate to a medical imaging device (e.g., an X-ray device) that includes a provisioning device according to the present embodiments. This, for example, enables the input data set or input data sets to be processed by the computer-implemented method according to the present embodiments immediately on acquisition or subsequently thereto (e.g., during the first visualization by an operator). However, alternatively to integration in the medical imaging device, the provisioning device may also be a separate device that receives input data and/or outputs output data (e.g., via a network, a database or an exchangeable data carrier).

In addition, the present embodiments relate to a computer program for a data processing device with program instructions that, when executed on the data processing device, execute the computer-implemented method according to the present embodiments for providing an output data set and/or the computer-implemented method according to the present embodiments for data processing in the context of medical subtraction imaging.

DETAILED DESCRIPTION

Figure 1:
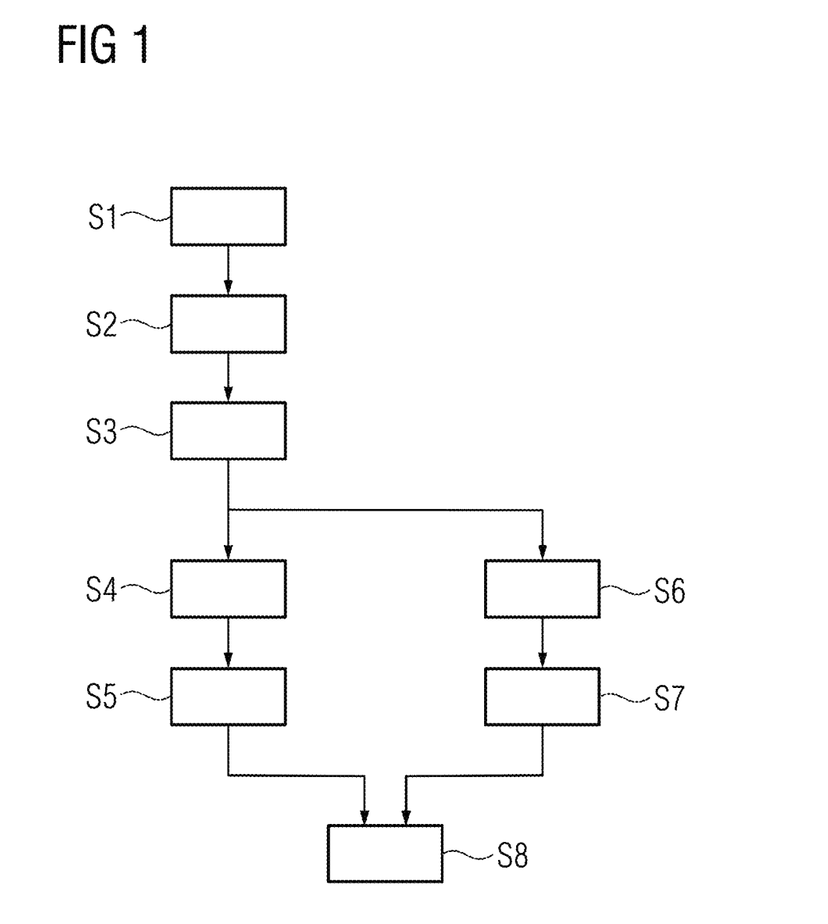
FIG. 1 shows a flowchart of an exemplary embodiment of a computer-implemented method for providing an output data set.

FIG. 1 shows a flowchart of one embodiment of a computer-implemented method for providing an output data set as a function of an input data set determined by a medical imaging method. The method is explained in the following with additional reference to FIG. 2, which is a schematic depiction of algorithms and data structures used in the context of the method. For reasons of clarity, in each case, two-dimensional individual image data sets are depicted as an input data set or as processing results. However, the described method is also suitable for processing three-dimensional image data sets. It is also possible for the input data set to include a plurality of image data sets recorded in sequence so that the processing results may accordingly also include a plurality of image data sets. This is also not depicted for reasons of clarity.

Figure 2:
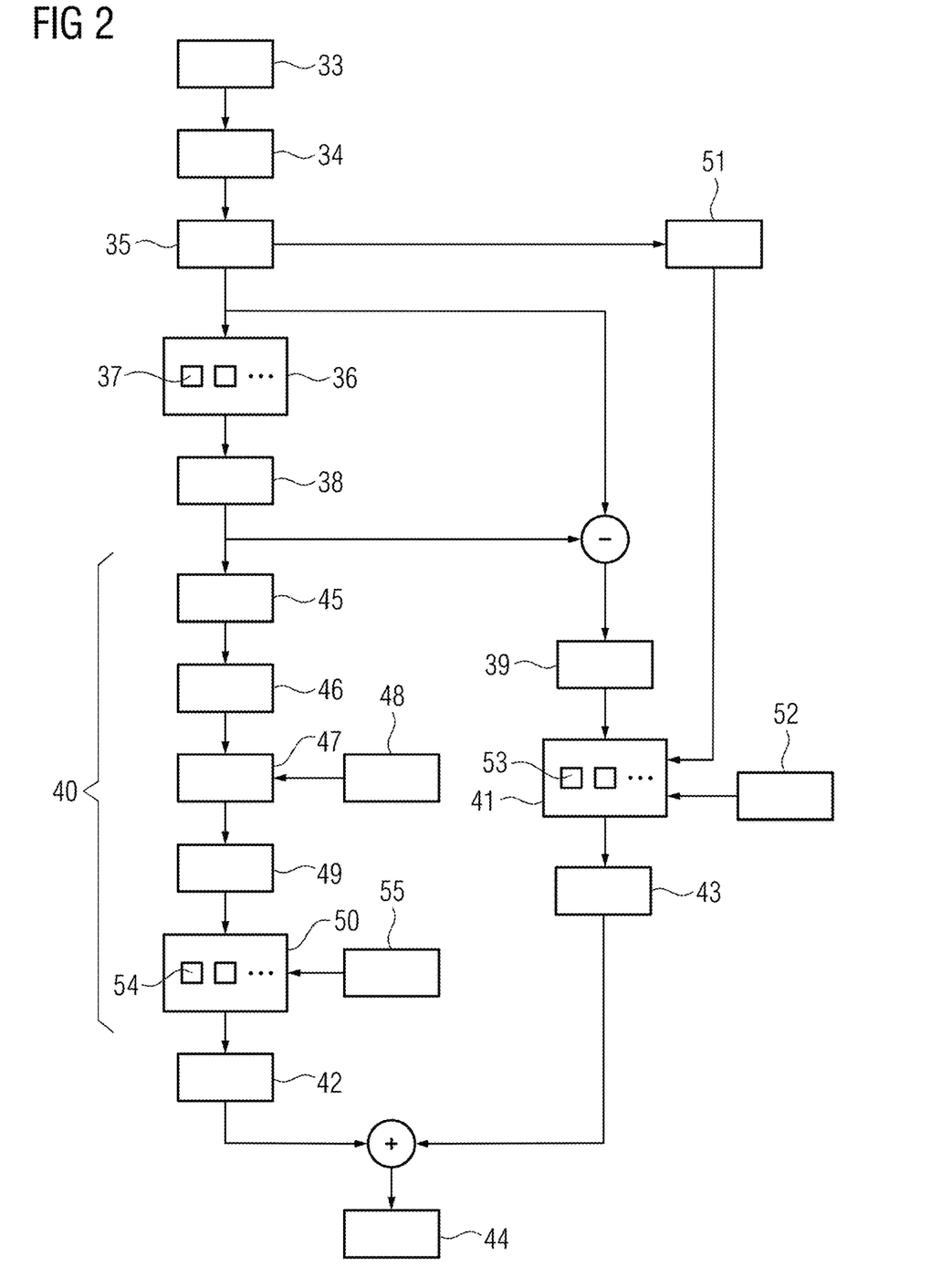
FIG. 2 shows exemplary algorithms and data structures used in the context of the method shown in FIG. 1.

In act S1, initially, an input data set 33 determined by a medical imaging method (e.g., as an X-ray recording with a flat-panel detector) is provided. The acquisition of the image data from the input data set may, for example, take place in an upstream step independently of the computer-implemented method explained. However, in principle, it would also be possible to integrate the acquisition in the method.

In act S2, a variance-stabilizing transformation 34 is applied to the input data set 33 in order to generate an intermediate data set 35. The variance-stabilizing transformation 34 serves to modify a noise component of the input data set such that the noise is substantially independent of the measuring signal (e.g., to transfer the noise from a Poisson distribution to a Gaussian distribution). Different approaches that are known per se may be used for the variance stabilization. For example, a root function or an Anscombe transformation may be applied to the image data from the input data set 33.

In act S3, an algorithm 36 for reducing image noise is applied to the intermediate data set 35 in order to determine the noise-reduced signal data set 38. Due to the upstream variance stabilization, it is possible to use any algorithm 36 suitable for reducing signal-independent noise. As will be explained later, the algorithm 36 may, for example, be trained by machine learning. For this purpose, the algorithm 36 may include a large number of free parameters 37, which are learned in the context of training. One option for training such an algorithm 36 will be explained later with reference to FIG. 5, and possible structures for corresponding algorithms will be explained later with reference to FIGS. 6 and 7.

In act S4, a noise data set is determined by subtracting the signal data set 38 from the intermediate data set 35. This substantially maps the noise in the intermediate data set 35 or the variance-stabilized noise in the input data set 33.

This is followed by parallel processing of the noise data set 39 in act S5 by a noise-processing algorithm 41 in order to provide a modified noise data set 43 and of the signal data set 38 in acts S6 and S7 in order to provide a modified signal data set 42. In act S8, the modified signal data set 42 and the modified noise data set 43 are subsequently added together in order to provide the output data set 44.

The application of the noise-processing algorithm 41 in act S5 may cause a scaling or shaping of the noise to take place such that the actual noise spectrum approximates a desired noise spectrum. In the simplest case, scaling of the entire noise data set would be possible. However, in one embodiment, different scaling of different frequency components of the noise data set 7 or filtering of the noise data set 39 takes place in order to bring the noise spectrum into line with a desired shape. For example, coloration of the noise that occurs due to the measuring electronics used may be eliminated or the like.

In the example, for this, different scaling factors 53 are used for the scaling of the frequency components. The noise data set 39 may be divided into frequency components, for example, via a Fourier transformation or by constructing a Gauss-Laplace pyramid with which Gaussian filters of different sizes are applied in different positions after which the differences of positions correspond to different frequency components.

For the adjustment of the noise, for example, at least one measure 51 for the noise is determined in the intermediate data set 35 or alternatively also in the input data set 33 or in the noise data set 39. For example, noise amplitudes may be determined for different frequency components. Approaches for determining such a measure 51 have already been discussed in the general part of the description.

Additionally, the scaling factors 53 or other parameters parameterizing the noise-processing algorithm 41 may be functions of additional information 52, which, for example, may relate to a user-defined function for noise adjustment, a water equivalent for the examination object, or other parameters relating to the imaging or evaluation of the image data and were already discussed above. The scaling factors 53 or parameters of the noise-processing algorithm 41 may, for example, be taken from a lookup table as a function of the parameters.

In act S6, initially, an inverse transformation 45 for variance-stabilizing transformation 34 is performed in the context of the signal processing algorithm 40. The variance-stabilizing transformation 34 causes the noise in the intermediate data set 35 to be substantially frequency-independent. However, in this case, the variance-stabilizing transformation 34 falsifies the signal component. This is compensated by applying the inverse transformation 45; as a result of this, the intermediate result 46 substantially corresponds to the signal component of the input data set 33.

In an alternative embodiment, the acts S2 and S6, the variance-stabilizing transformation 34 and the inverse transformation 45, may also be dispensed with. In this case, the input data set 33 may be used in each case instead of the intermediate data set 35, and the processing in act S7 may process the signal data set 38 directly instead of the intermediate result 46.

In act S7, the contrast processing of the intermediate result 46 or, if variance stabilization is dispensed with, of the signal data set 38 takes place. In this case, gray level transformations and spatial frequency operations may be applied, for example. For example, lookup tables, bandpass filters, multi-scalar filters, etc. may be used. In the example shown, the application of a non-linear function 47 in order to determine a further intermediate result 49 and the subsequent application of a function 50 for contrast adjustment to the further intermediate result 49 to determine the modified signal data set 42 are performed in sequence.

The non-linear function 47 is, for example, modified as a function of a predicted contribution 48 of scattered radiation to the image data from the signal data set 38 or the processing result 46. This, for example, serves to compensate an offset of the signal data set 38 or the intermediate result 46 due to these scattered rays. Alternatively, it would also be possible to modify the intermediate result 46 before applying the non-linear function 15. The application of a non-linear function (e.g., a logarithmic function) may serve to provide that that the same thickness differences of the mapped object with the same materials always result in the same changes in contrast, and this may greatly facilitate the evaluation of the image data.

The function 50 for contrast adjustment may, for example, be a function of parameters 54 that may, for example, be functions of output variables 55 of dose regulation used in the context of the medical imaging method. The parameters 54 may, for example, be determined using a lookup table, a prespecified functional connection, or the like.

The function 50 may, for example, weight different frequency components in the further intermediate result differently in order, for example, to highlight fine structures or the like.

In the example discussed with reference to FIGS. 1 and 2, both the signal data set 38 and the noise data set 39 are modified before addition to the output data set 44. In principle, it would also be possible only to modify one of these data sets and to leave the other one unchanged.

Figure 3:
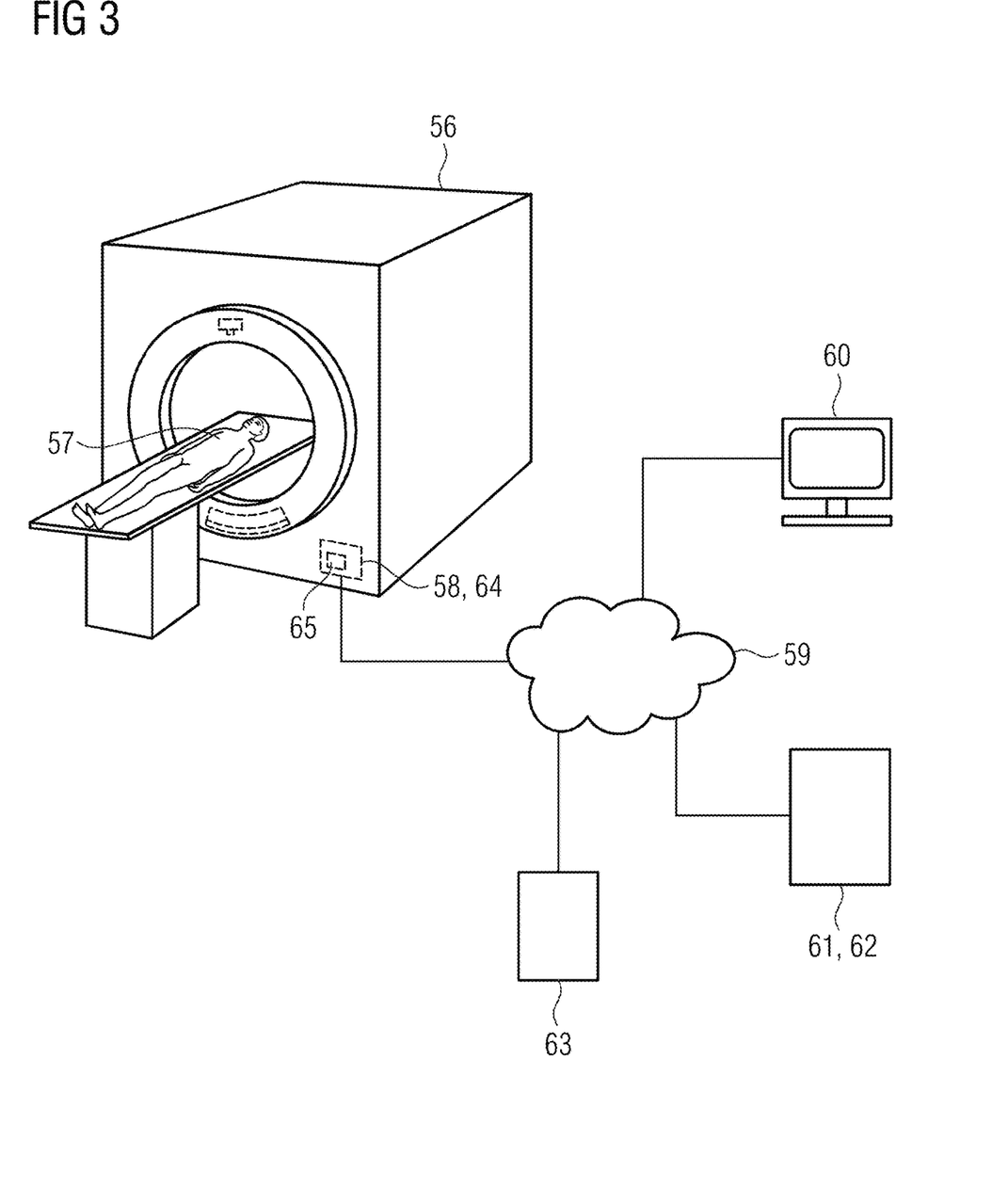
FIG. 3 shows an interaction of an exemplary embodiment of a provisioning device with a medical imaging device.

FIG. 3 shows one embodiment of a medical imaging device 56 (e.g., an X-ray device), by which the input data set 33 in the previously explained method, which maps the examination object 57, may be acquired. A control device 58

(e.g., a controller) controls the operation of the imaging device 56. The control device 58 may, for example, implement dose regulation 65, which controls the X-ray dose irradiated onto the examination object 57 as a function of acquired measurement data (e.g., as a function of a contrast-to-noise ratio for a defined object).

The control device 58 may in principle provide the input data set determined directly (e.g., via the network 59) to an evaluation device 60 (e.g., a workstation computer). However, in this case, there may be significant differences with regard to the contrasts or noise that occur for different examination objects, different angulation angles, etc., for example, due to the use of dose regulation 65, thus complicating evaluation of the image data.

Therefore, the input data set 33 acquired is initially transferred to the provisioning device 61, which implements the method explained above with reference to FIGS. 1 and 2. This may, for example, take place in that a data processing device 62 is appropriately programed by an appropriate computer program. The resulting output data set 44 may then, for example, be provided to the evaluation device 60.

The input data sets 33 or output data sets 44 may also be initially buffered in a database 63, thus enabling the described data processing to take place independently of the acquisition of the measurement data by the medical imaging device 56. If, in this case, as explained above, operating parameters of the medical imaging device 56 (e.g., parameters of dose regulation 65) are taken into account, the operating parameters may be filed jointly with the input data set 33 in the database 63.

For example, the depicted use of a provisioning device 61 embodied separately from the medical imaging device 56 enables the explained method to be offered as a service. However, in some cases, it may also be advantageous, instead of a separate provisioning device 61, to use a provisioning device 64 integrated in the medical imaging device 56, which may, for example, be implemented by the control device 58. This enables the advantages of the explained method to be used independently of external devices.

Figure 4:
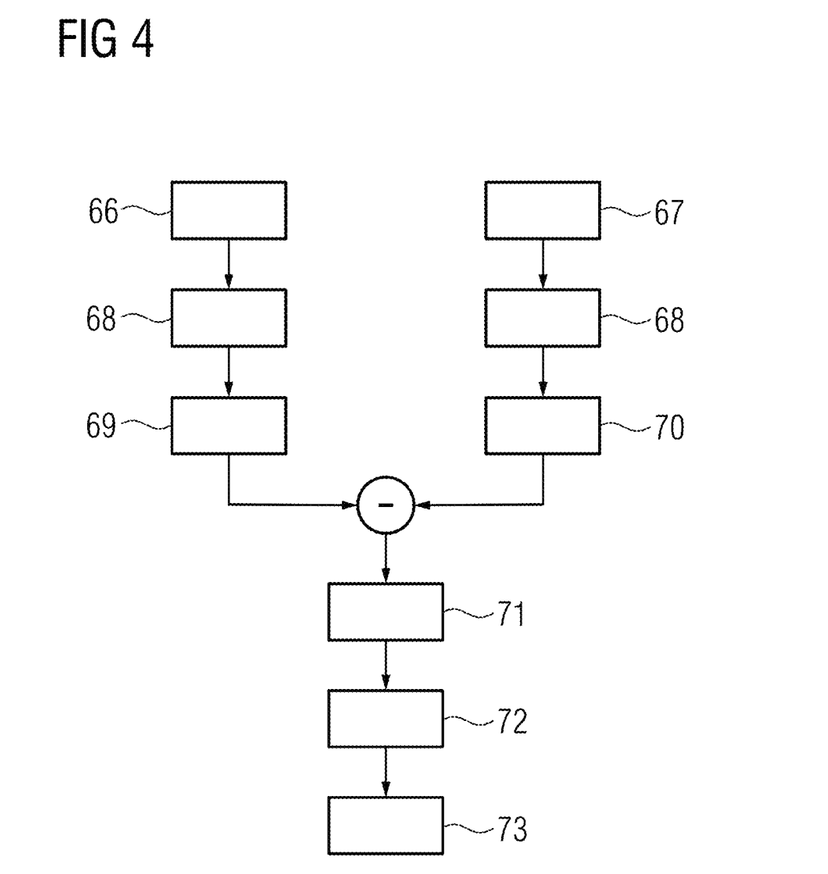
FIG. 4 shows exemplary algorithms and data structures used in the context of an exemplary embodiment of a computer-implemented method for data processing in the context of medical subtraction imaging.

FIG. 4 shows an exemplary embodiment of a computer-implemented method for data processing in the context of medical subtraction imaging. In this case, two input data sets 66, 67 are each processed by the method 68 already explained with reference to FIGS. 1 and 2 for providing a respective output data set 69, 70. The output data sets 69, 70 are then subtracted from one another in order to provide the subtraction data set 71. Then, a function 72 for contrast adjustment is applied to the image data from the subtraction data set 71 in order to a provide a contrast-adjusted subtraction data set 73.

In the method 68, in contrast to the variant depicted in FIG. 2, in act S7, the function 50 for contrast adjustment may not be applied; instead, the function 72 is used for contrast adjustment and is only applied when the output data sets 69, 70 have been subtracted from one another. This may avoid different impacts of the function 50 on the output data sets 69, 70 that falsify the subtraction data set 71. In this case, it is accepted that, in the context of contrast adjustment, the function 72 for contrast adjustment in the exemplary embodiment shown in FIG. 4 also varies the noise component of the subtraction image 71.

Apart from the fact that it is used at a different point in time in the method, the function 72 for contrast adjustment may correspond to the function 50 for contrast adjustment already discussed with reference to FIG. 2. Accordingly, the parameters of function 72 may also be varied as a function of imaging parameters or other parameters, as has already been explained with regard to FIG. 2 and function 50.

Figure 5:
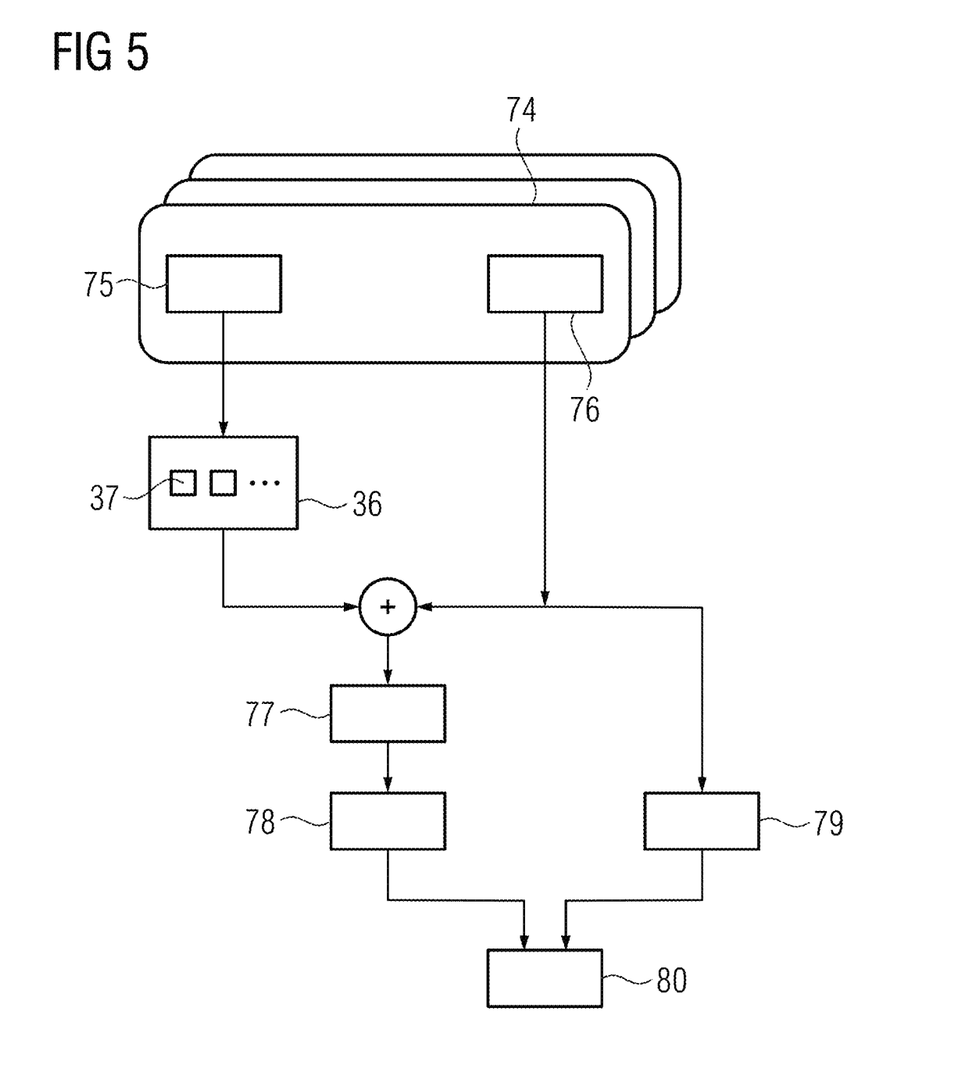
FIG. 5 shows an exemplary embodiment of a training method for training an algorithm for reducing image noise that may be used in the context of the computer-implemented methods by a machine-learning method.

FIG. 5 shows an exemplary training method for training the algorithm 36 for reducing the image noise, which may be used in the context of the computer-implemented method according to the present embodiments, using a machine-learning method. The algorithm is trained using training data sets 74 each including a first image data set 75 and a second image data set 76. The first image data set 75 and the second image data set 76 are acquired on the same examination object with the same acquisition parameters.

For the training of the algorithm 36, a cost function 80 is minimized by varying the parameters 37 of the algorithm 36. The cost function 80 is a function of a difference between a measure 79 for the noise in the second image data set 76 and a measure 78 for the noise in a sum data set 77. The sum data set 77 is determined in that the algorithm to be trained 36 is applied to the first image data set 75 and the resulting result data set is added to the second image data set 76. The variation of the parameters 37 of the algorithm 36 may, for example, take place using an error feedback method that is known per se.

Figure 6:
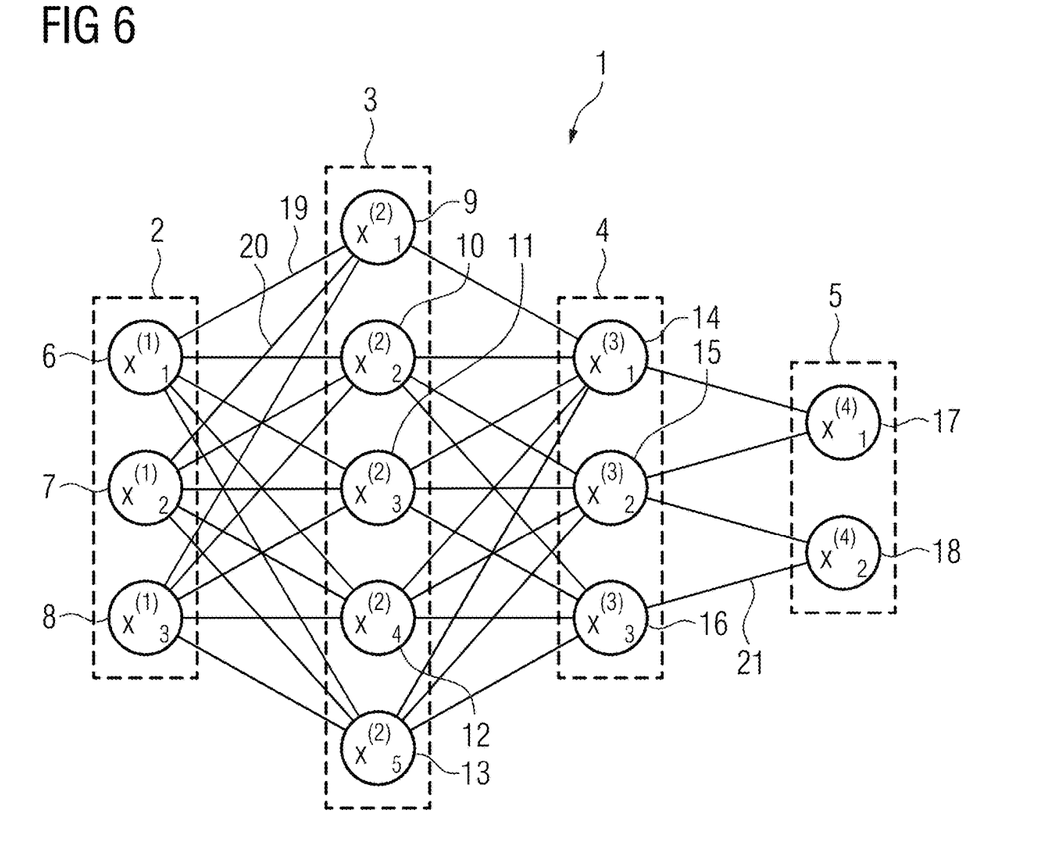
FIGS. 6 and 7 show exemplary structures of algorithms that may be trained to reduce image noise.
Figure 7:
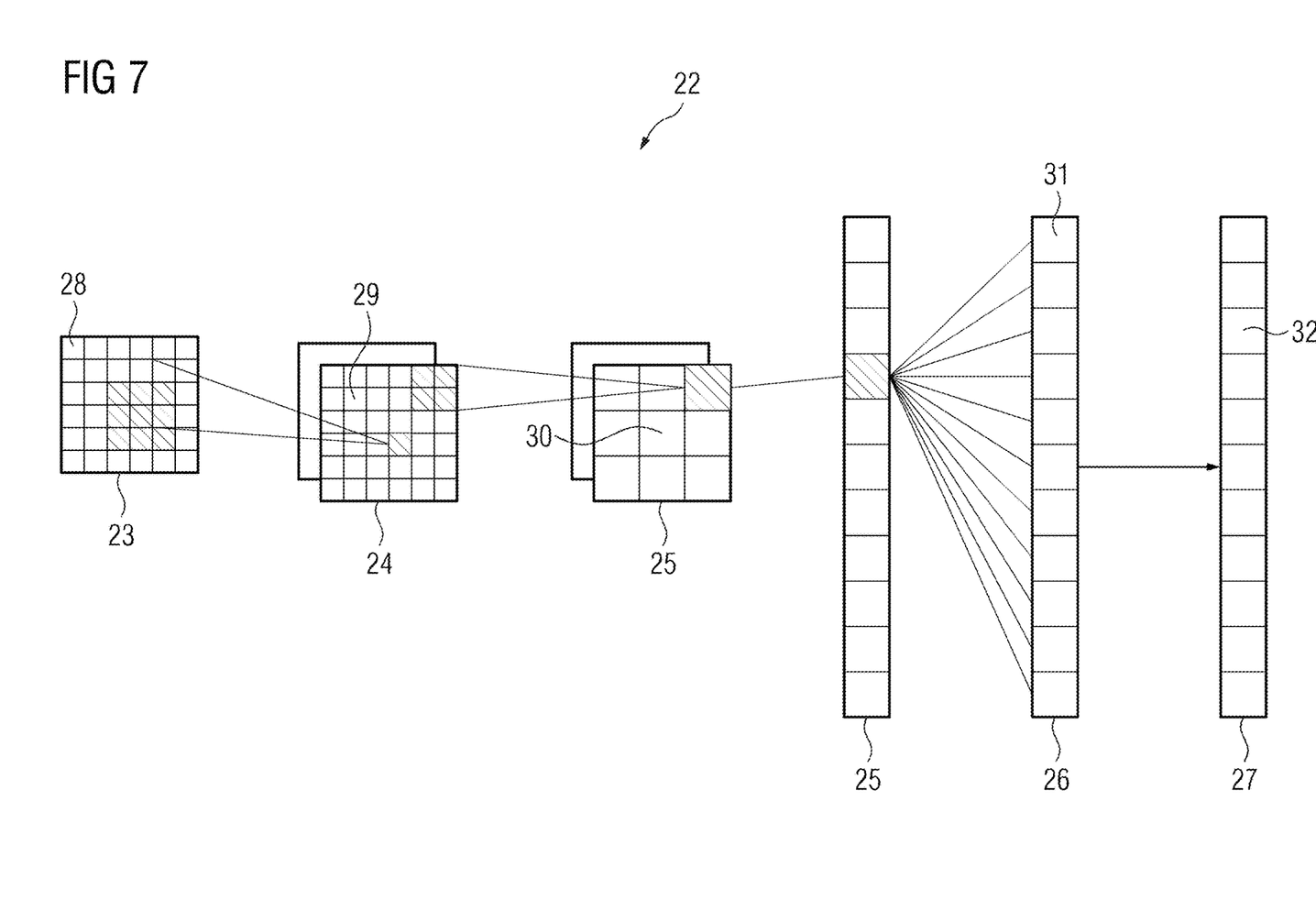

With reference to FIGS. 6 and 7, the following uses the example of a neural network or a convolutional neural network to explain structures of algorithms that may be trained by machine learning in order to provide the algorithm 36 for reducing image noise. The structures are described using simple examples that may be expanded appropriately for real applications.

FIG. 6 shows an exemplary embodiment of an artificial neural network 1. Other English expressions for artificial neural network 1 are "neural network", "artificial neural net", or "neural net".

The artificial neural network 1 includes nodes 6 to 18 and edges 19 to 21, where each edge 19 to 21 is a directional link from a first node 6 to 18 to a second node 6 to 18. Generally, the first node 6 to 18 and the second node 6 to 18 are different nodes 6 to 18; however, the first node 6 to 18 and the second node 6 to 18 may be identical. For example, in FIG. 6, the edge 19, a directional link from the node 6 to node 9 and the edge 21, is a directional link from the node 16 to the node 18. An edge 19 to 21 from a first node 6 to 18 to a second node 6 to 18 is referred to as an ingoing edge for the second nodes 6 to 18 and as an outgoing edge for the first node 6 to 18.

In this exemplary embodiment, the nodes 6 to 18 of the artificial neural network 1 may be arranged in layers 2 to 5, where the layers 2 to 5 may have an intrinsic order, which is introduced through the edges 19 to 21 between the nodes 6 to 18. For example, edges 19 to 21 may only be provided between adjacent layers of nodes. In the exemplary embodiment depicted, there is an input layer 2 that only has the nodes 6, 7, 8, in each case without an ingoing edge. The output layer 5 includes only the nodes 17, 18, in each case without outgoing edges, where there are hidden layers 3 and 4 between the ingoing layer 2 and the output layer 5. Generally, the number of hidden layers 3, 4 may be chosen as desired. The number of nodes 6, 7, 8 in the input layer 2 may correspond to the number of input values into the neural network 1, and the number of nodes 17, 18 in the output layer 5 may correspond to the number of output values of the neural network 1.

For example, a real number may be assigned to the nodes 6 to 18 of the neural network 1. Herein, $x^{(m)}_i$ designates the value of the i-th nodes 6 to 18 in the n-th layer 2 to 5. The values of the nodes 6, 7, 8 in the input layer 2 are equivalent to the input values of the neural network 1, while the values of the nodes 17, 18 in the output layer 113 are equivalent to the output values of the neural network 1. Moreover, a weight in the form of a real number may be assigned to each edge 19, 20, 21. For example, the weight is a real number in the interval [−1, 1] or in the interval [0, 1,]. Herein, $w^{(m,n)}_{i,j}$ designates the weight of the edge between the i-th nodes 6 to 18 in the m-th layer 2 to 5 and the j-th nodes 6 to 18 in the n-th layer 2 to 5. Further, the abbreviation $w_{i,j}^{(n)}$ is defined for the weight $w_{i,j}^{(n,n+1)}$.

In order to calculate output values of the neural network 1, the input values are propagated by the neural network 1. For example, the values of the nodes 6 to 18 in the (n+1)-th layer 2 to 5 may be calculated based on the values of the nodes 6 to 18 of the n-th layer 2 to 5 by $$x_j^{(n+1)} = f(\Sigma_i x_i^{(n)} \cdot w_{i,j}^{(n)}).$$

Herein, f is a transfer function, which may also be designated an activation function. Known transfer functions are step functions, sigmoid functions (e.g., the logistic function, the generalized logistic function, the hyperbolic tangent, the arcus tangent, the error function, the smoothstep function), or rectifier functions. The transfer function is substantially used for purposes of standardization.

For example, the values are propagated in layers by the neural network 1, where values of the ingoing layer 2 are defined by the input data of the neural network 1. Values of the first hidden layer 3 may be calculated based on the values of the ingoing layer 2 of the neural network 1, values of the second hidden layer 4 may be calculated based on the values in the first hidden layer 3, and so on.

In order to be able to establish the values $w_{i,j}^{(n)}$ the edges 19 to 21, the neural network 1 is to be trained using training data. For example, training data includes input training data and output training data, which are designated $t_i$ below. For a training step, the neural network 1 is applied to the input training data in order to determine calculated output data. For example, the output training data and the calculated output data include a number of values, where the number is determined as the number of nodes 17, 18 in the output layer 5.

For example, a comparison between the calculated output data and the output training data is used in order to adjust the weights within the neural network 1 recursively (e.g., back propagation algorithm). For example, the weights may be changed according to $$w'^{(n)}_{i,j} = w^{(n)}_{i,j} - \gamma \cdot \delta_j^{(n)} \cdot x_i^{(n)},$$

where γ is a learning rate, and the numbers $\delta_j^{(n)}$ may be calculated recursively as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta_j^{(n+1)}$, when the (n+1)-th layer is not the output layer 5 and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)-th layer is the output layer 5, where f is the first derivation of the activation function and $y_j^{(n+1)}$ is the comparison training value for the j-th node 17, 18 in the output layer 5.

The following also defines an example of a convolutional neural network (CNN) with respect to FIG. 7. Herein, it should be noted that the expression "layer" is used there in a slightly different manner than for conventional neural networks. For a conventional neural network, the expression "layer" only refers to the set of nodes that forms a layer (e.g., a specific generation of nodes). For a convolutional neural network, the expression "layer" is often used as an object that actively changes data (e.g., a set of nodes of the same generation and either the set of ingoing edges or the set of outgoing edges).

FIG. 7 shows an exemplary embodiment of a convolutional neural network 22. In the exemplary embodiment, the convolutional neural network 22 includes an ingoing layer 23, a convolutional layer 24, a pooling layer 25, a fully connected layer 26, and an output layer 27. In alternative embodiments, the convolutional neural network 22 may contain a plurality of convolutional layers 24, a plurality of pooling layers 25, and a plurality of fully connected layers 26, plus other types of layers. The sequence of layers may be selected at will, where fully connected layers 26 form the last layers before the output layer 27.

For example, within a convolutional neural network 22, the nodes 28 to 32 in one of the layers 23 to 27 may be arranged as d-dimensional matrix or as d-dimensional image. For example, in the two-dimensional case, the value of a node 28 to 32 with the indices i, j may be designated $x^{(n)}[i,j]$ in the n-th layer 23 to 27. Reference is made to the fact that the arrangement of the nodes 28 to 31 in a layer 23 to 27 has no impact on the calculations within the convolutional neural network 22 as such since this impact is exclusively defined by the structure and weights of the edges.

A convolutional layer 24 is, for example, characterized in that the structure and the weights of the ingoing edges form a convolution operation based on a specific number of kernels. For example, the structure and weights of the ingoing edges may be selected such that the values $x_k^{(n)}$ of the nodes 29 in the convolutional layer 24 are determined as a convolution $x_k^{(n)} = K_k * x^{(n-1)}$ based on the values $x^{(n-1)}$ of the nodes 28 in the preceding layer 23, where, in the two-dimensional case, the convolution * may be defined as $$x_k^{(n)}[i,j] = (K_k * x^{(n-1)})[i,j] = \Sigma_{i'} \Sigma_{j'} K_k[i',j'] \cdot x^{(n-1)}[i-i',j-j'].$$

Here, the k-th kernel $K_k$ is a d-dimensional matrix (e.g., a two-dimensional matrix) that is usually small compared to the number of nodes 28 to 32 (e.g., a 3×3-matrix or a 5×5-matrix). For example, this implies that the weights of the ingoing edges are not independent, but are selected such the weights generate the above convolution equation. In the example of a kernel that forms a 3×3-matrix, there are only nine independent weights (e.g., where each entry in the kernel matrix corresponds to an independent weight), regardless of the number of nodes 28 to 32 in the corresponding layer 23 to 27. For example, for a convolutional layer 24, the number of nodes 29 in the convolutional layer 24 is equivalent to the number of nodes 28 in the preceding layer 23 multiplied by the number of convolution kernels.

If the nodes 28 in the preceding layer 23 are arranged as a d-dimensional matrix, the use of the plurality of kernels may be understood to be the addition of a further dimension, which is also designated a depth dimension, so that the nodes 29 in the convolutional layer 24 are arranged as a (d+1)-dimensional matrix. If the nodes 28 in the preceding layer 23 are already arranged as a (d+1)-dimensional matrix with a depth dimension, the use of a plurality of convolution kernels may be understood as an expansion along the depth dimension so that the nodes 29 in the convolutional layer 221 are likewise arranged as a (d+1)-dimensional matrix, where the size of the (d+1)-dimensional matrix in the depth dimension is greater than in the preceding layer 23 by the factor formed by the number of kernels.

The advantage of using convolutional layers 24 is that the spatially local correlation of the input data may be exploited in that a local connection pattern between nodes in adjacent layers is created (e.g., due to the fact that each node only has connections to a small region of the nodes in the preceding layer).

In the exemplary embodiment, the ingoing layer 23 includes nodes 28 arranged as a two-dimensional 6×6-matrix. The convolutional layer 24 includes 72 nodes 29 arranged as two two-dimensional 6×6-matrices, where each of the two matrices is the result of a convolution of the values of the ingoing layer 23 with a convolution kernel. In the same way, the nodes 29 in the convolutional layer 24 may be understood as being arranged in a three-dimensional 6×6×2-matrix, where the last-named dimension is the depth dimension.

A pooling layer 25 is characterized in that that the structure and weights of the ingoing edges and the activation function of their nodes 30 define a pooling operation based on a non-linear pooling function f. For example, in the two-dimensional case, the values $x^{(n)}$ of the nodes 30 in the pooling layer 25 may be calculated based on the values $x^{(n+1)}$ of the nodes 29 in the preceding layer 24 as $$x^{(n)}[i,j]=f(x^{(n-1)}[id_1,jd_2], \ldots, x^{(n-1)}[id_1+d_1-1, jd_2+d_2-1]).$$

In other words, the use of a pooling layer 25 may reduce the number of nodes 29, 30 in that a number of $d_1 * d_2$ adjacent nodes 29 in the preceding layer 24 is replaced by one single node 30, which is calculated as a function of the values of the stated number of adjacent nodes 29. For example, the pooling function f may be a maximum function, an averaging, or the L2 norm. For example, for a pooling layer 25, the weights of the ingoing edges may be fixed and not modified by training.

The advantage of using a pooling layer 25 is that the number of nodes 29, 30 and the number of parameters is reduced. This results in a reduction in the number of calculations required within the convolutional neural network 22 and hence to suppression of overfitting.

In the exemplary embodiment depicted, the pooling layer 25 is a max pooling layer, in which four adjacent nodes are replaced by one single node, the value of which is formed by the maximum of the values of the four adjacent nodes. The max pooling is applied to each d-dimensional matrix of the previous layer; in this exemplary embodiment, the max pooling is applied to each of the two two-dimensional matrices so that the number of nodes is reduced from 72 to 18.

A fully connected layer 26 is characterized in that that a plurality (e.g., all) of the edges between the nodes 30 in the previous layer 25 and the nodes 31 in the fully connected layer 26 are present, where the weight of each of the edges may be adjusted individually. In this exemplary embodiment, the nodes 30 of the layer 25 preceding the fully connected layer 26 are shown as both two-dimensional matrices and as non-linked nodes (e.g., depicted as a row of nodes, where the number of nodes has been reduced to improve the depiction). In this exemplary embodiment, the number of nodes 31 in the fully connected layer 26 is equal to the number of nodes 30 in the preceding layer 25. In alternative embodiments, the number of nodes 30, 31 may differ.

In this exemplary embodiment, the values of the nodes 32 in the output layer 27 are determined in that the softmax function is applied to the values of the nodes 31 in the preceding layer 26. As a result of the application of the softmax function, the sum of the values of all nodes 32 in the output layer 27 is one and all values of all the nodes 32 in the output layer are real numbers between 0 and 1. If the convolutional neural network 22 is used to classify input data, for example, the values of the output layer 27 may be interpreted as a probability that the input data falls into one of the different classes.

A convolutional neural network 22 may also have a ReLU layer, where ReLU stands for "rectified linear units". For example, the number of nodes and the structure of the nodes within a ReLU layer is equivalent to the number of nodes and the structures of the nodes in the preceding layer. The value of each node in the ReLU layer may, for example, be calculated by applying a rectifier function to the value of the corresponding nodes in the preceding layer. Examples of rectifier functions are $f(x)=\max(0,x)$, hyperbolic tangent, or the sigmoid function.

Convolutional neural networks 22 may, for example, be trained based on the back-propagation algorithm. To avoid overfitting, regularization methods may be used (e.g., dropout of individual nodes 28 to 32, stochastic pooling, the use of artificial data, weight decay based on the L1 or L2 norm, or maximum norm restrictions).

Although the invention has been illustrated and described in detail by the exemplary embodiments, the invention is not restricted by the disclosed examples, and other variations may be derived herefrom by the person skilled in the art without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for providing an output data set as a function of an input data set that is determined by a medical imaging method, the computer-implemented method comprising:
   determining a noise-reduced signal data set, the determining of the noise-reduced signal data set comprising applying an algorithm for reducing image noise to the input data set or an intermediate data set determined as a function of the input data set;
   determining a noise data set as a difference between the input data set or the intermediate data set and the noise-reduced signal data set;
   determining a modified noise data set, wherein the determining of the modified noise data set comprises applying a noise-processing algorithm to the noise data set, or applying the noise-processing algorithm to the noise data set and determining a modified signal data set, wherein determining the modified signal data set comprises applying a signal processing algorithm to the noise-reduced signal data set; and
   determining an output data set, determining the output data set comprising adding the modified noise data set to the noise-reduced signal data set or the modified signal data set or adding the noise data set to the modified signal data set,
wherein the noise-processing algorithm is a function of an imaging parameter, an object parameter of an examination object, an output variable of a dose regulation, or any combination thereof.

2. The computer-implemented method of claim 1, wherein the noise-processing algorithm includes scaling of the noise data set, different scaling of different frequency components of the noise data set, or filtering of the noise data set.

3. The computer-implemented method of claim 2, further comprising determining at least one measure for a noise in the input data set, the intermediate data set, or the noise data set,
wherein the noise-processing algorithm is a function of the at least one measure for the noise.

4. The computer-implemented method of claim 3, further comprising determining a scaling factor for the scaling of the noise data set or scaling factors for the different scaling of the different frequency components, determining a parameter of the filtering as a function of the at least one measure for the noise, or a combination thereof.

5. The computer-implemented method of claim 1, further comprising determining the intermediate data set, the determining of the intermediate data set comprising applying a variance-stabilizing transformation to the input data set,
wherein the signal processing algorithm is or includes an assigned inverse transformation.

6. The computer-implemented method of claim 1, further comprising applying, in the context of the signal processing algorithm, a non-linear function to image data from the signal data set or image data of a processing result that is determined in the context of preprocessing within the signal processing algorithm as a function of the signal data set.

7. The computer-implemented method of claim 6, wherein the non-linear function is a logarithmic function.

8. The computer-implemented method of claim 6, further comprising predicting a contribution from scattered radiation that occurs during acquisition of the input data set to the image data from the signal data set or predicting the processing result,
wherein the non-linear function is a function of the predicted contribution, or the signal data set or the intermediate result is corrected before the application of the non-linear function as a function of the predicted contribution.

9. The computer-implemented method of claim 1, further comprising applying, in the context of the signal processing algorithm, a function for contrast adjustment to an image data from the signal data set or image data of one or a further processing result that is determined in the context of preprocessing within the signal processing algorithm as a function of the signal data set.

10. The computer-implemented method of claim 1, wherein the signal processing algorithm, the noise-processing algorithm, or the signal processing algorithm and the noise-processing algorithm are parameterized as a function of at least one input parameter, at least one output variable, or the at least one input parameter and the at least one output variable of a dose regulation used in the context of the medical imaging method.

11. The computer-implemented method of claim 1, wherein the algorithm used as the algorithm for reducing the image noise is trained by a machine-learning method.

12. A provisioning device configured to provide an output data set as a function of an input data set, the provisioning device comprising:
a processor configured to:
determine the intermediate data set, the determination of the intermediate data set comprising application of a variance-stabilizing transformation to the input data set;
determine a noise-reduced signal data set, the determination of the noise-reduced signal data set comprising application of an algorithm for reducing image noise to the input data set or the intermediate data set determined as a function of the input data set;
determine a noise data set as a difference between the input data set or the intermediate data set and the noise-reduced signal data set;
determine a modified noise data set, wherein the determination of the modified noise data set comprises application of a noise-processing algorithm to the noise data set, or application of the noise-processing algorithm to the noise data set and determination of a modified signal data set, wherein the determination of the modified signal data set comprises application of a signal processing algorithm to the noise-reduced signal data set; and
determine an output data set, the determination of the output data set comprising adding the modified noise data set to the noise-reduced signal data set or the modified signal data set or adding the noise data set to the modified signal data set,
wherein the signal processing algorithm is or includes an assigned inverse transformation.

13. A medical imaging device comprising:
a provisioning device configured to provide an output data set as a function of an input data set, the provisioning device comprising:
a processor configured to:
determine a noise-reduced signal data set, the determination of the noise-reduced signal data set comprising application of an algorithm for reducing image noise to the input data set or an intermediate data set determined as a function of the input data set;
determine a noise data set as a difference between the input data set or the intermediate data set and the noise-reduced signal data set;
determine a modified noise data set, wherein the determination of the modified noise data set comprises application of a noise-processing algorithm to the noise data set, or application of the noise-processing algorithm to the noise data set and determination of a modified signal data set, wherein the determination of the modified signal data set comprises application of a signal processing algorithm to the noise-reduced signal data set; and
determine an output data set, the determination of the output data set comprising adding the modified noise data set to the noise-reduced signal data set or the modified signal data set or adding the noise data set to the modified signal data set,
wherein the signal processing algorithm, the noise-processing algorithm, or the signal processing algorithm and the noise-processing algorithm are parameterized as a function of at least one input parameter, at least one output variable, or the at least one input parameter and the at least one output variable of a dose regulation used in the context of a configuration of the medical imaging device.

14. The medical imaging device of claim 13, wherein the medical imaging device is an X-ray device.

15. In a non-transitory computer-readable storage medium that stores instructions executable by one or more processors to provide an output data set as a function of an input data set that is determined by a medical imaging method, the instructions comprising:
- determining a noise-reduced signal data set, the determining of the noise-reduced signal data set comprising applying an algorithm for reducing image noise to the input data set or an intermediate data set determined as a function of the input data set;
- determining a noise data set as a difference between the input data set or the intermediate data set and the noise-reduced signal data set;
- determining at least one measure for a noise in the input data set, the intermediate data set, or the noise data set;
- determining a modified noise data set, wherein the determining of the modified noise data set comprises applying a noise-processing algorithm to the noise data set, or applying the noise-processing algorithm to the noise data set and determining a modified signal data set, wherein determining the modified signal data set comprises applying a signal processing algorithm to the noise-reduced signal data set, and wherein the noise-processing algorithm includes scaling of the noise data set, different scaling of different frequency components of the noise data set, or filtering of the noise data set;
- determining a scaling factor for the scaling of the noise data set or scaling factors for the different scaling of the different frequency components, determining a parameter of the filtering as a function of the at least one measure for the noise, or a combination thereof; and
- determining an output data set, determining the output data set comprising adding the modified noise data set to the noise-reduced signal data set or the modified signal data set or adding the noise data set to the modified signal data set,
- wherein the noise-processing algorithm is a function of the at least one measure for the noise.

* * * * *